United States Patent [19]

Oser

[11] 4,200,939
[45] May 6, 1980

[54] METHOD FOR FIXATION OF PROSTHESES TO BONE

[75] Inventor: Zale Oser, Bound Brook, N.J.

[73] Assignee: Codman & Shurtleff, Inc., Randolph, Mass.

[21] Appl. No.: 843,754

[22] Filed: Oct. 19, 1977

[51] Int. Cl.² .............................................. A61F 1/00
[52] U.S. Cl. .................................... 3/1.9; 128/334 R
[58] Field of Search ................... 3/1, 1.9, 1.91, 1.911, 3/1.912, 1.913; 128/90, 926, 334 R

[56]  References Cited
U.S. PATENT DOCUMENTS

| 2,155,658 | 4/1939 | Herrmann et al. | 424/78 |
| 3,030,951 | 4/1962 | Mandarino | 128/92 G |
| 3,483,876 | 12/1969 | Coover, Jr. et al. | 128/334 R |
| 3,524,537 | 8/1970 | Winter | 128/334 R X |
| 3,656,184 | 4/1972 | Chambers | 3/1 |
| 3,692,023 | 9/1972 | Phillips et al. | 128/90 |
| 3,968,791 | 7/1976 | Forsberg | 128/90 |

OTHER PUBLICATIONS

*Howmedica*; Technical Monograph, "Surgical Simplex P Radiopague Bone Cement", 10 pages; Oct. 1971.
New Product Information Bulletin F–44221 (Union Carbide), "Polycaprolactone Polymer PCL–700"; 4 pages, Nov. 1972.
New Product Information Bulletin F–44453 (Union Carbide), "Polycaprolactone Polymer PCL–700 Biodegradation and Molding Information"; 4 pages, Jul. '73.
J. Biomed. Mater. Res. Symposium (1975); Haas et al., "A Proposed Specification for Acrylic Bone Cement", pp. 105–117; 1975.

*Primary Examiner*—Clifford D. Crowder
*Attorney, Agent, or Firm*—Alice O. Robertson; Leonard P. Prusak

[57]  ABSTRACT

Method for fixation of prostheses to bone with sterile non toxic polymers such as polycaprolactone which are formable viscous liquids or putty-like solids at temperatures within the range of 45°–75° C. and hard, rigid solids at temperatures below about 42° C., and to a sterile package containing such polymers.

4 Claims, No Drawings

METHOD FOR FIXATION OF PROSTHESES TO BONE

BACKGROUND OF THE INVENTION

1. Field of the Invention

This invention relates to the surgical fixation of prostheses in fractured, diseased and necrotic bones. More specifically, it concerns the use of sterile, biocompatible, non-biodegradable, high molecular weight, atoxic, inelastic, thermoplastic polymers which melt at ranges of from about 45° C. and are rigid solids below about 42° C. for fixation of prostheses to bone in surgical procedures of the hip joint, in osteoarthritis, rheumatoid arthritis, traumatic arthritis, avascular necrosis, non-union of fractures of neck and femur, sickle cell anemia, revision of previous arthroplasty procedures, fractures of the neck of the femur in the elderly suitable for prosthetic replacement, and unstable fractures in individuals with metastatic malignancies.

2. Description of the Prior Art

The fixation of endoprostheses in calcified tissue plays an important role in orthopedic surgery. Ideally, products used for this purpose should have handling characteristics and physical and chemical properties which are peculiarly suitable for this purpose. For example, the material should not adhere to the surgeon's glove when it is ready to be used and it should be easy to apply in the presence of moisture and set soon after without dimensional changes or the generation of excess heat.

Most importantly, a material for use in fixing prostheses into bone should be biocompatible, nonabsorbable, rigid at body temperatures, sterilizable, have a low level of histotoxicity and lack carcinogenicity.

A number of polymeric compositions have been used by surgeons in recent years for fixing prostheses into bone, the most widely used being polymethyl methacrylate. However, many difficulties are associated with this material, both with respect to the surgeon and the patient. Since the monomer is highly volatile and flammable, the operating room must be provided with adequate air circulation. In practice, the monomer must be admixed with methyl methacrylate-styrene copolymer to give it the desired cementitious characteristics. During the mixing, caution must be exercised to prevent excessive exposure to the vapors of the monomer which may produce irritation of the respiratory tract, eyes and possibly liver.

Another disadvantage of methyl methacrylate is its property as a powerful lipid solvent. It should not be allowed to come into direct contact with sensitive tissues or be absorbed by the body since the monomer is suspected of being toxic. Furthermore, the uncontrolled heat rise resulting from the polymerization reaction may cause necrosis of the bone.

Other materials recommended for use in bone fixation include various derivatives of alpha-cyanoacrylate such as methyl alpha-cyanoacrylate, monomeric alkoxyalkyl 2-cyanoacrylate, alpha-cyanoacrylate esters and compositions containing these substances together with other additives including polymers. Like the polymethyl methacrylates, the use of these materials requires the introduction of monomers into the bone area, and the monomers polymerize in situ to form a permanent, polymeric composition.

This invention provides a method for fixing prosthetic devices into bone tissue which is simple, convenient, atoxic to surgeon and patient, and reversible. It eliminates the present need for conducting polymerization reactions in situ, avoids the preparation of the compositions requiring volatile monomers or solvents, and affords the opportunity to remove the prosthesis at any time by the simple application of heat within a temperature range which is not dangerous to the patient.

SUMMARY

In accordance with the method of the present invention, a biocompatible, preformed, thermoplastic polymer having a melting point within the range of from about 45° C. to 75° C., and which is a rigid solid at body temperatures is employed to secure an artificial prosthesis in a bone member. The bone member is prepared to receive the prosthesis in a conventional manner as, for example, when using a polymethyl methacrylate cement. The thermoplastic polymer of the present invention is warmed until it becomes soft and moldable, and is packed into the prosthesis receiving opening in the bone member. The prosthesis is then inserted into the bone while the polymer is still soft, and excess polymer which extrudes from the opening is removed. The prosthesis is held immobile until the polymer cools and hardens after which the operation is concluded in a conventional manner. Should it become necessary to remove the prosthesis, heat is applied gently to the prosthesis until the surrounding polymer softens after which the prosthesis may be easily withdrawn.

DESCRIPTION OF PREFERRED EMBODIMENTS

In a specific embodiment of my invention, a biocompatible, non-absorbable, preformed polymer whose melting point is from about 45° C. to about 75° C. and which is a rigid solid at body temperatures below about 42° C. is placed in a standard Toomey-type disposable syringe with a wide aperture and appropriate capacity of about 50–100 milliliters. The filled syringe is placed in a peel-apart package for sterile delivery and sterilized with cobalt radiation or heat, the former being preferred. Alternatively, the polymer can be placed in a squeeze bottle of suitable capacity and having a slit orifice.

In actual use, the surgeon's aid simply peels apart the sterile package, and using sterile techniques heats the syringe in an autoclave to melt the polymer and prepare the material for application. While in the molten state, the polymer is expressed into the prepared cavity of the intermedullary canal of the open bone and the prosthesis is inserted. Alternatively, it may be ejected from the syringe in molten form into cool sterile water to create a workable mass suitable for digital application into, for example, the acetabulum or femur. Whether the surgery involves the joint of the hip, knee, or elbow, a similar procedure is conducted on the end of the adjoining bone. Within a short period of time, about five minutes, the cooled polymer becomes a tough, rigid mass and the surgeon concludes the operation.

Although the preferred method of the present invention is directed to the use of a single homopolymer or a copolymer, it is conceivable that a mixture of polymers chosen specifically to obtain a low melting point eutectic composition may also be employed.

A wide range of polymers which fulfill the physical and chemical characteristics required for the method of this invention may be employed, the preferred polymer being polycaprolactone, a known substance available commercially from the Union Carbide Corporation and described in its new product information bulletin F44221, Polycaprolactone Polymer PCL-700.

The polymers useful in the method of the present invention preferably have minimum strength characteristics at least as great as those of present acrylic bone cements. The proposed ASTM specification for esters of methacrylic acid to be used as bone cements as reported in *J. Biomed. Mater. Res. Symp.* 6, 105–117 (1975) include the following mechanical properties determined at 25° C. in accordance with the procedure set forth in that article:

| | | |
|---|---|---|
| Compressive strength, MPa | 80 | min. |
| Indentation, mm | 0.11 | max. |
| Recovery, % | 60 | min. |

The preferred polymer of the present invention, polycaprolactone, has the following corresponding properties at 25° C.

| | |
|---|---|
| Compressive strength, MPa | 19,300 |
| Indentation, mm | 0.089 |
| Recovery, % | 84.4 |

Polycaprolactone is a linear polyester formed through the ring opening of the monomer epsilon-caprolactone. Polycaprolactone is a crystalline thermoplastic resin which can be readily molded at moderate temperatures to yield tough transluscent products. Its crystalline melting point is about 60° C., which represents a theoretical upper temperature limit of use for the present invention. Above its melting point the material is characterized by a high degree of conformability and workability. Additional polymers which are suitable for use in the method of this invention are the following:

RIGID THERMOPLASTIC MATERIALS WITH MELT RANGES From 45° C.–75° C.

| Class of Polymer | Polymer Structure | Supplier and No. |
|---|---|---|
| Polyurethane | MDI + OH terminated polycaprolactone ester | K. J. Quinn PA 93 |
| | MDI + OH terminated polycaprolactone + adipate esters | K. J. Quinn PA 01 |
| | MDI + adipate ester | Hooker Chemical P-250 |
| | MDI + adipate ester + OH chain extender (small chain glycol) | Mobay Chemical Desmocoll E4 39T |
| Polyurethane | TDI + OH terminated adipate ester | Mobay Chemical Desmocoll 400T |
| | MDI + OH terminated adipate ester | B. F. Goodrich Chemical Estane 5711 |
| Polyamide | C$_{36}$ Dimer (saturated) acid + ethylene diamine + caprolactam | Emery Industries EM 1553 |

TDI = Toluene-2,4-Di isocyanate
MDI = Methylene bis (4 phenyl isocyanate)

Other polymers such as poly(dodecene-1) and tran-spolyisoprene are also useful in this invention. All of these polymers are characterized by being crystalline at room temperature, non-crystalline at about 70° C. and having a relatively rapid rate of crystallization when cooled to body temperature. These polymers do not crystallize like simple compounds so that there is a reasonable time lag after the polymer reaches body temperature before crystallization is complete. This permits sufficient time for the prosthesis to be positioned in the bone member while the polymer is still pliable.

If desired, substances such as antibiotics, antibacterial agents, and antifungal agents may also be admixed with the polymer. Examples of antimicrobial agents which may be employed include tetracycline, oxytetracycline, chlorotetracycline, neomycin, erithromycin, and its derivative, bacitracin, streptomycin, rifampicin and its derivatives such as N-dimethylrifampicin, kanamycin and chloromycetin. Useful antifungal agents include griseofulvin, mycostatin, miconazole and its derivatives as described in U.S. Pat. No. 3,717,655; bisdiguanides such as chlorhexidine; and more particularly quaternary ammonium compounds such as domiphen bromide, domiphen chloride, domiphen fluoride, benzalkonium chloride, cetyl pyridinium chloride, dequalinium chloride, the cis isomer of 1-(3-chlorallyl)-3,5,7-triaza-1-azoniaadamantane chloride (available commercially from the Dow Chemical Company under the trademark Dowicil 200) and its analogues as described in U.S. Pat. No. 3,228,828 cetyl trimethyl ammonium bromide as well as benzethonium chloride and methylbenzethonium chloride such as described in U.S. Pat. Nos. 2,170,111, 2,115,250 and 2,229,024; the carbanilides and salicylanilides such 3,4,4'-trichlorocarbanilide, and 3,4'5-tribromosalicylanilide; the hydroxydiphenyls such as dichlorophene, tetrachlorophene, hexachlorophene, and 2,4,4'-trichloro- 2'-hydroxydiphenylether; and organometallic and halogen antiseptics such as sinc pyrithione, silver sulfadiazone, silver uracil, iodine, and the iodophores derived from non-ionic surface active agents such as are described in U.S. Pat. Nos. 2,710,277 and 2,977,315 and from polyvinylpyrrolidone such as described in U.S. Pat. Nos. 2,706,701, 2,826,532 and 2,900,305.

TOXICITY STUDIES

Male, Swiss Webster mice, weighing 22–28 grams, were used in this study. The animals were acclimated for one week prior to use, and were housed in groups of 5 mice per cage. They were allowed free access to food and water at all times.

To reduce the pellets of PCL-700 polycaprolactone to a fine powder, the material was ground with dry ice in a high speed micro mill (Janke & Kunkel) and then passed through a #80 sieve. A 15% (w/v) suspension of polycaprolactone was prepared in 2% pectin solution (0.9% saline).

The maximum dose tested by both the intraperitoneal (IP) and subcutaneous (SC) routes was 10 g/kg; therefore, the control mice in the IP group received 67 ml/kg of 2% pectin. Animals were examined frequently the day of dosing and daily thereafter for 14 days. At this time the survivors were killed and examined for gross pathologic changes.

The LD$_{50}$ of PCL-700 when given IP or SC was greater than 10 g/kg. The doses tested and results are summarized:

| Route | PCL-700 Dose | Mortality |
|---|---|---|
| IP | 5 g/kg | 0/10 |
| | 10 g/kg | 0/10 |
| IP | None (2% Pectin) | 0/10 |

| Route | PCL-700 Dose | Mortality |
|---|---|---|
| SC | (67 ml/kg) 10 g/kg | 0/10 |

At necropsy, inspection of peritoneal cavities of mice given polycaprolactone revealed numerous deposits of powder. Some were off white with thin walled capsules, others tan with thicker walled capsules. These were variously adherent to liver, pancreas, stomach, spleen, intestine and mesentery. The anterior surfaces of the livers had patchy cloudy areas, and portions of the liver were tenaciously adherent to the diaphragm.

There were no apparent toxic effects following subcutaneous injection of 10 g/kg of polycaprolactone. At necropsy, the powder in the subcutis was contained in a moderately thick walled capsule, and the adjacent tissues appeared normal.

The only overt symptoms noted following intraperitoneal injection of polycaprolactone were occasional episodes of varying degrees of abdominal twisting and stretching. The treated mice had a 3 to 9% body weight loss the first 2 days after injection, whereas the control mice (2% pectin) gained weight. Thereafter, the weight gains of experimental animals were similar to those of the controls.

HYDROLYSIS STUDIES

The hydrolysis of polycaprolactone in sodium phosphate buffer, pH 7.25, was investigated up to 100 days at 37.5° C. Approximately 0.2 g of the polymer is placed in a 250 ml Erlenmeyer flask containing 200 ml of sterile buffer solution. It was then capped and placed in the incubator maintained at 37.5° C. Similarly, three more samples were prepared for various time periods and placed in the incubator. At the end of each time period, the flask was taken out and the polymer was isolated by filtration, washed several times with distilled water, and it was then dried overnight under vacuum. The final weight of the dry polymer was measured and the percent weight loss calculated. To follow the extent of hydrolysis of the polymer, the inherent viscosities were measured at the end of each period in chloroform (0.1 g/dl) at 25° C. The results are summarized below.

| Sample No. | Time, Days | Weight Loss | I.V. |
|---|---|---|---|
| 1 | 0 | — | 0.94 |
| 2 | 21 | 0% | 0.88 |
| 3 | 62 | 0.17% | — |
| 4 | 100 | 0.95% | 0.80 |
| 5 | 204 | 1.7% | 0.68 |

About 1% weight loss is observed at the end of 100 days. There is a 15% decrease in I.V. during this period, indicating some degradation of the polymer chain. Even after 204 days, only a small percent of weight loss was observed and no significant change in the physical state of the polymer was observed visually, i.e., the polymer pellets were intact.

What is claimed is:

1. In a method for securing an artificial prothesis within a bone member wherein the prosthesis is inserted into a cavity in the bone member and permanently secured therein with a void filling, cementitious composition, the improvement comprising filling the void space around the prosthesis within the cavity of the bone member with said cementitious composition consisting essentially of a formable, thermoplastic polymer at a temperature in the range of 45° to 75° C. and thereafter allowing the polymer to cool to a hard, rigid solid at body temperature whereby the prosthesis is firmly secured within said bone member.

2. A method in accordance with claim 1 wherein the polymer is characterized by the following mechanical properties at 25° C.:

| Compressive strength, MPa | 80 | min. |
|---|---|---|
| Indentation, mm | 0.11 | max. |
| Recovery, % | 60 | min. |

3. A method in accordance with claim 1 wherein the polymer is polycaprolactone.

4. A method in accordance with claim 1 wherein the polymer is poly(dodecene-1).

* * * * *